United States Patent [19]

Atkinson et al.

[11] 4,056,536
[45] Nov. 1, 1977

[54] PYRROLO[2,1-b][3]BENZAZEPINES

[75] Inventors: Joseph G. Atkinson, Montreal; Patrice C. Belanger, Dollard des Ormeaux; Clarence S. Rooney, Beaconsfield, all of Canada; Susan F. Britcher, Norristown, Pa.

[73] Assignee: Merck & Co., Inc., Rahway, N.J.

[21] Appl. No.: 700,921

[22] Filed: June 29, 1976

[51] Int. Cl.$^2$ .......................................... C07D 487/04
[52] U.S. Cl. .................. 260/326.5 B; 260/326.29; 260/326.47; 260/326.5 J; 260/326.5 S; 260/326.5 SF; 260/326.31; 542/415; 542/471
[58] Field of Search ............... 260/326.5 B, 326.5 S, 260/326.5 SF, 326.31

[56] References Cited
PUBLICATIONS

Cooper et al., Tet. Letters 45, 4321–4324 (1971).
Huisgen et al., Chem. Ber. 93, 65–81 (1960).
Weinstein et al., J. Organic Chem. 41, 875–878 (1976).

*Primary Examiner*—Donald G. Daus
*Assistant Examiner*—Mark L. Berch
*Attorney, Agent, or Firm*—William H. Nicholson; Harry E. Westlake, Jr.

[57] ABSTRACT

11H-Pyrrolo[2,1-b][3]benzazepin-11-one and derivatives thereof are generally prepared by Friedel-Crafts ring closure of a N-styrylpyrrole-2-carboxylic acid derivative. They are useful intermediates in the synthesis of skeletal muscle relaxants and tranquilizers such as 11-(3-dimethylaminopropylidene)-2-cyano-11H-pyrrolo[2,1-b][3]benzazepine.

7 Claims, No Drawings

PYRROLO[2,1-b][3]BENZAZEPINES

BACKGROUND OF THE INVENTION

Over the past several years several so-called tricyclic compounds such as amitriptyline, cyclobenzaprine, nortriptyline and protriptyline have gained importance as centrally acting pharmacological agents. Now with the present invention, there is provided compounds from which new tricyclic compounds can be prepared which have skeletal muscle relaxant and tranquilizing activity.

Thus, it is an object of the present invention to provide compounds of structural formula:

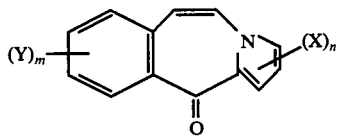

It is a further object to provide processes for the preparation of the compounds.

DETAILED DESCRIPTION OF THE INVENTION

In particular, this invention relates to compounds of structural formula:

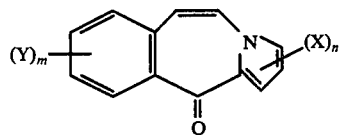

wherein
$n$ is 3, 2, 1, or 0 (X is hydrogen);
$m$ is 4, 3, 2, 1 or 0 (Y is hydrogen); and
X and Y are independently selected from
(1) hydrogen,
(2) halo, such as chloro, bromo, fluoro, or iodo,
(3) formyl,
(4) lower alkanoyl, especially $C_{2-6}$ alkanoyl such as acetyl, pentanoyl, or 2-methylpropanoyl,
(5) lower alkyl, especially $C_{1-5}$ alkyl, either straight or branched chain, such as methyl, propyl, or pentyl,
(6) lower alkoxycarbonyl, especially ($C_{1-5}$ alkoxy)-carbonyl,
(7) hydroxy-lower alkyl, especially hydroxy-$C_{1-3}$-alkyl,
(8) perhalo-lower alkyl, especially perhalo-$C_{1-3}$-alkyl, such as trifluoromethyl,
(9) lower alkoxy, especially $C_{1-3}$ alkoxy, such as methoxy or propoxy,
(10) cyano,
(11) perhalo-lower alkylthio, especially perhalo-$C_{1-3}$ alkylthio, such as trifluoromethylthio,
(12) lower alkylthio, especially $C_{1-3}$ alkylthio, such as methylthio or propylthio,
(13) lower alkylsulfonyl, especially $C_{1-3}$ alkyl sulfonyl, such as methylsulfonyl or isopropylsulfonyl,
(14) perhalo-lower alkylsulfonyl, especially perhalo-$C_{1-3}$ alkylsulfonyl, such as trifluoromethylsulfonyl,
(15) lower alkylsulfinyl, especially $C_{1-3}$ alkylsulfinyl, such as methylsulfinyl,
(16) perhalo-alkylsulfinyl, especially perhalo-$C_{1-3}$-alkylsulfinyl, such as trifluoromethylsulfinyl,
(17) amino,
(18) lower alkanoylamino, especially $C_{2-6}$ alkanoylamino, such as acetylamino, or pentanoylamino,
(19) lower alkylamino, especially $C_{1-3}$ alkylamino,
(20) di(lower alkyl)amino, especially di($C_{1-3}$ alkyl)-amino,
(21) hydroxy,
(22) N-lower alkylcarbamoyl, especially N-$C_{1-3}$ alkylcarbamoyl,
(23) N,N-di(lower alkyl)carbamoyl, especially N,N-di($C_{1-3}$ alkyl)carbamoyl,
(24) nitro,
(25) di(lower alkyl)sulfamoyl, especially di($C_{1-3}$-alkyl)sulfamoyl,
(26) lower alkoxycarbonylamino, especially $C_{1-3}$ alkoxycarbonylamino,
(27) N-lower alkylcarbamoyloxy, especially $C_{1-3}$-alkylcarbamoyloxy,
(28) carboxy, and
(29) carbamoyl.

One embodiment of the novel compounds of this invention is that wherein $n$ is 2, 1, or 0 (X is hydrogen) and X is in the 2 and/or 3 position.

Another embodiment of the novel compounds is that wherein $m$ and $n$ are independently 1 or 0.

A preferred embodiment of the novel compounds of this invention is the compound of structural formula:

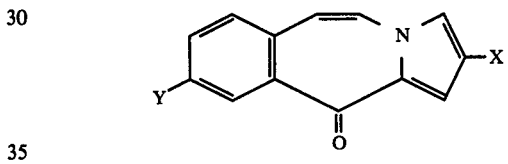

A still more preferred embodiment of the novel compounds is where one of X and Y is hydrogen, and the other is cyano or formyl.

The novel compounds of the present invention are generally prepared by a modified Friedel-Crafts reaction wherein the catalyst is preferably stannic chloride and the starting material is a cis-N-styrylpyrrole-2-carboxylic acid trifluoroacetic acid mixed anhydride. The process comprises mixing a cis-N-styrylpyrrole-2-carboxylic acid with trifluoracetic anhydride for 5–30 minutes at room temperature in a usual Friedel-Crafts solvent such as methylene chloride and adding stannic chloride at 0°–25° C. The reaction is complete in about 10–30 minutes.

An alternative process, useful where the pyrrole ring carries a strong electron withdrawing group such as cyano comprises dehydrohalogenation of a 6-halo-6,11-dihydro-5H-pyrrolo [2,1-b]benzazepin-11-one by treatment with a strong base such as sodium hydroxide or potassium hydroxide in a lower alkanol, such as ethanol at 25°–100° C. for 10–30 minutes.

A third process comprises dehalogenation of a 5,6-dihalo-6,11-dihydro-5H-pyrrolo[2,1-b][3]benzazepin-11-one by treatment with chromous chloride in aqueous acetone at 25°–80° C. for 5–30 minutes.

3-Trifluoromethylthio-ketones are prepared by treatment of a novel ketone of this invention unsubstituted in the pyrrole ring with trifluoromethylsulfenyl chloride in an inert organic solvent such as chloroform, 1,1,2,2-tetrachloroethane or the like in the presence of an acid acceptor such as pyridine at 30° C. to reflux temperature for 1–5 hours.

The novel ketones carrying a trifluoromethylthio or alkylthio group on the benzo ring are prepared by treating the corresponding bromo- or iodo- compound with trifluoromethylthiocopper or cuprous alkylsulfide respectively. The reaction is conducted in a mixture of quinoline and pyridine at about 200° C. for 6–24 hours.

The novel compounds, wherein the substituent X is 2-acyl, such as acetyl, dimethylsulfamoyl, or the like, are prepared by acylation of a novel ketone unsubstituted in the pyrrole ring with the appropriate acid chloride such as acetyl chloride or dimethylsulfamoyl chloride or the like in the presence of a Friedel-Crafts catalyst such as aluminum chloride in an inert solvent such as methylene chloride, 1,1,2,2-tetrachloroethane, nitromethane or the like at −20° C. to 150° C. for 5 minutes to about 3 hours.

The alkanoyl derivatives described above may also be prepared by treating the ketone with an excess of alkanoyl chloride without the Friedel-Crafts catalyst and without the inert solvent. A mixture of the 2, and 3-alkanoyl ketones are obtained which are separated by chromatography on silica gel to provide the 3-alkanoyl compounds.

Formyl-6,11-dihydro-5H-pyrrolo[2,1-b][3]benzazepin-11-ones may be prepared by reduction of the corresponding cyano compound with nickel-aluminum alloy in formic acid or aqueous formic acid at from 50° C. to reflux temperature for 30 minutes to 5 hours.

The carbamoyl substituted ketones may be prepared by hydrolysis of cyano ketones with a strong mineral acid such as hydrochloric acid in acetic acid at 50° C. to reflux temperature for 1–5 hours.

Carboxy-ketones may be prepared by diazotization of the corresponding carbamoyl-ketones with sodium nitrite in a strong mineral acid, such as aqueous sulfuric acid.

Alkyl-, and di(alkyl)carbamoyl ketones may be prepared from the corresponding carboxy ketones by forming the acid chloride therefrom followed by treatment with an alkylamine or a di(alkyl)amine in an inert organic solvent such as methylene chloride or the like, at −20° C. to reflux temperature until the reaction is complete.

Alkoxycarbonyl ketones may be prepared by heating at 50° C. to reflux for 1–8 hours the corresponding carboxy ketone in a lower alkanol in the presence of a strong mineral acid, such as hydrogen chloride.

Novel compounds with a trifluoromethylthio substituent in the benzo ring may be prepared by reacting the corresponding iodo- or bromo- ketone with trifluoromethylthiocopper formed by the reaction of copper powder with bis(trifluoromethylthio)mercury in a polar organic solvent such as dimethylformamide, quinoline, or hexamethylphosphoramide at 50° C. to 200° C. for 0.5–24 hours.

Similarly, an alkylthio or cyano group may be introduced into the benzo- ring employing cuprous methylsulfide or cuprous cyanide respectively in place of the copper powder and bis(trifluoromethylthio)mercury.

Hydroxymethyl ketones are prepared by reduction of formyl ketones preferably with sodium borohydride in a lower alkanol at 10°–40° C.

Trifluoromethyl ketones may be prepared by treatment of the corresponding carboxy ketone with sulfur tetrafluoride in a pressure vessel at 75°–150° C. for 2–12 hours followed by treatment with alkali.

Sulfinyl and sulfonyl-ketones are prepared by hydrogen peroxide oxidation of the corresponding thiocompounds by art recognized procedures.

Hydroxy-ketones are prepared by dealkylation of the corresponding alkoxy-ketone, preferably by treatment with sodium ethyl sulfide in an inert organic solvent such as dimethylformamide at reflux temperature.

Carbamoyl-ketones are prepared by mineral acid hydrolysis of the corresponding cyano-ketone, which in turn may be diazotized to the corresponding carboxy-ketones by standard procedures.

Ethoxycarbonylamino-ketones are prepared by treating the corresponding carboxy compound with diphenylphosphoroazide in ethanol in the presence of triethylamine at reflux for 1–6 hours.

Alkaline hydrolysis of the above ethoxycarbonylamino compounds with sodium or potassium hydroxide in refluxing alcohol provides the corresponding amino compound.

Alkylation and acylation of the amino ketones provides the alkyl-, dialkyl- and acyl-amino ketones of this invention.

The novel compounds of this invention are useful intermediates for the synthesis of skeletal muscle relaxants and tranquilizers of structural formula:

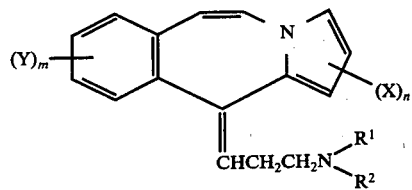

wherein X, Y, m, and n are as previously defined and $R^1$ and $R^2$ are independently selected from hydrogen, lower alkyl, or alkenyl which may be straight chain, branched chain, or cyclic, or may be joined together to form groups such as 1-piperidyl, 1-pyrrolidyl or 4-morpholinyl.

The skeletal muscle relaxants preparable from the novel compounds of this invention are administered in the usual pharmaceutical unit dosage forms, preferably orally at the rate of 0.1 to 30 mg./kg. of body weight per day. As tranquilizers, these compounds are administered at the rate of 0.1 to 30 mg./kg. of body weight per day.

The pharmacologically active compounds are preparable from the novel compounds of this invention in accordance with the following chemical equation which is exemplified by the synthesis of 2-cyano-11-(3-dimethylaminopropylidene)-11H-pyrrolo[2,1-b][3]benzazepine.

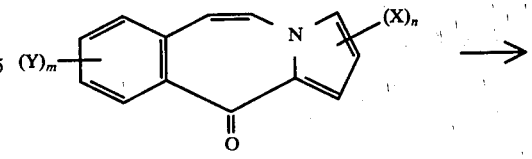

-continued

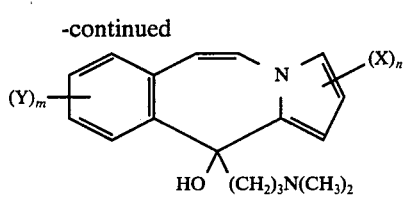

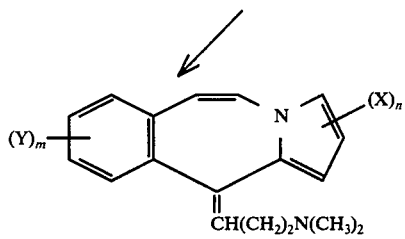

Preparation of 2-cyano-11-(3-dimethylaminopropylidene)-11H-pyrrolo[2,1-b][3]benzazepine A mixture of 4 g. of 2-cyano-11H-pyrrolo[2,1-b]-[3]benzazepin-11-one in 50 ml. of tetrahydrofuran is treated dropwise with 20 ml. of tetrahydrofuran containing 28.40 mmole of 3-(dimethylamino)propylmagnesium chloride while maintaining the temperature at 25° C. Ten minutes after the addition is complete, 2 ml. of water is added and the mixture is poured into 200 ml. of methylene chloride, dried over sodium sulfate and filtered. Concentration to dryness provides 3.3 g. (60%) of a solid residue of 2-cyano-11-(3-dimethylaminopropyl)-11-hydroxy-11H-pyrrolo[2,1-b][3]-benzazepine, m.p. 123°–126° C.

A mixture of 2.8 g. of the 11-hydroxy compound in 50 ml. of chloroform is treated with hydrogen chloride gas for 5 minutes while maintaining the temperature at 25° C. The mixture is neutralized with 2 N sodium hydroxide and extracted twice with chloroform. The extract is washed with water, dried and concentrated to dryness to give 2.4 g. of oil.

The oil is dissolved in 10 ml. of acetonitrile and treated with 1.0 g. of oxalic acid. After 4 hours at room temperature and overnight in the refrigerator, the solids are collected, washed with ether and air dried to give 2.7 g. of 2-cyano-11-(3-dimethylaminopropylidene)-11H-pyrrolo[2,1-b][3]benzazepine, oxalate, m.p. 185°–187° C. (dec.).

The methods of synthesis and use of the skeletal muscle relaxants is more fully described and claimed by Rokach et al. in concurrently filed U.S. Pat. Application Ser. No. 701,001, with Attorney's Docket No. 14985IA, which is a continuation-in-part of U.S. Ser. No. 592,436, filed July 2, 1975 now abandoned.

EXAMPLE 1

2-Cyano-11H-pyrrolo[2,1-b][3]benzazepin-11-one

Step A: Preparation of trans-2-carboxy-4-cyano-N-styrylpyrrole

A mixture of 5 g. of sodium hydride and 15 g. of methyl 4-cyanopyrrole-2-carboxylate, in 75 ml. of dimethyl formamide was stirred until evolution of hydrogen ceased. Styrene oxide (16 g.) was added and heated at 110° C. for 6 hours. The mixture was poured into 300 ml. of water and extracted with 2 × 150 ml. of ether. The aqueous phase was purged with nitrogen and acidified with 2 N hydrochloric acid. The precipitated solid is collected, washed with water, air dried and washed with ether to give 6.4 g. of pure trans-2-carboxy-4-cyano-N-styrylpyrrole, m.p. 195°–196° C. (decarboxylation).

The sodium hydride used in the above step can be replaced by an equimolecular amount of potassium t-butoxide.

Step B: Preparation of cis-2-carboxy-4-cyano-N-styrylpyrrole

A solution of 50 mg. of trans-2-carboxy-4-cyano-N-styrylpyrrole in 1 ml. of acetonitrile was irradiated with a 450 watt lamp for 45 minutes. The solution was concentrated to dryness. The residue was triturated with ether and the product was collected and air dried to give 37 mg. of cis-2-carboxy-4-cyano-N-styrylpyrrole, m.p. 166°–168° C.

Following the procedure substantially as described in Example 1, Steps A and B, but substituting for the methyl 4-cyanopyrrole-2-carboxylate and styrene oxide used in Step A thereof, equimolecular amounts of the methyl pyrrole carboxylates and styrene oxides, respectively, depicted in Table I, there are produced the trans- and cis-N-styrylpyrrole-2-carboxylic acids, also depicted in Table I by the following process.

Table I

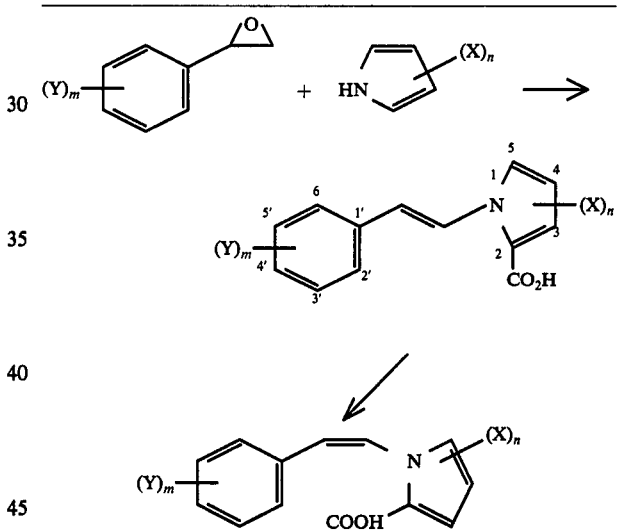

| Compound | $(Y)_m$ | $(X)_n$ |
|----------|---------|---------|
| 1 | H | H |
| 2 | H | 4-SCF$_3$ |
| 3 | 4'-Cl | H |
| 4 | 4'-SCF$_3$ | H |
| 5 | 4'-CN | H |
| 6 | H | 4-COCH(CH$_3$)$_2$ |
| 7 | H | 4-SO$_2$N(CH$_3$)$_2$ |
| 8 | H | 4-SO$_2$CH(CH$_3$)$_2$ |
| 9 | H | 4-Cl |
| 10 | 4'-Br | H |
| 11 | H | 4-NO$_2$ |
| 12 | 4'-OCH$_3$ | H |
| 13 | 4'-CF$_3$ | H |

Step C: Preparation of 2-cyano-11H-pyrrolo[2,1-b][3]benzazepin-11-one

A solution of 35 mg cis-2-carboxy-4-cyano-N-styrylpyrrole in 0.5 ml. of dry methylene chloride was treated with 45 μl. of trifluoroacetic anhydride and stirred for 5 minutes. Stannic chloride (45 μl.) was added and the mixture stirred for 15 minutes. The mixture was poured into water, neutralized with ammonium hydroxide and extracted twice with chloroform. The extract was washed with water, dried over sodium sulfate, and concentrated to dryness. Trituration of the residue with 0.5 ml. of ethyl acetate and filtering gave 2-cyano-11H-pyrrolo[2,1-b][3]benzazepin-11-one, m.p. 197° C.

Following the procedure substantially as described in Example 1, Step C, but substituting for the cis-2-carboxy-4-cyano-N-styrylpyrrole used therein, an equimolecular amount of the cis-styrylpyrroles from Table I, there are produced the 11H-pyrrolo[2,1-b][3]benzazepin-11-ones described in Table II, by the following process:

Step C: Preparation of 2-cyano-5,6-dichloror-6,11-dihydro-5H-pyrrolo-[2,1-b][3]benzazepin-11-one Aluminum chloride (231 mg.) was added all at once to a mixture of 160 mg. of 4-cyano-N-(1,2-dichloro-2-phenylethyl)pyrrole-2-carbonyl chloride and 0.5 ml. of tetrachloroethane controlled at 140° C. After 4–5 minutes, the mixture is cooled, 15 ml. of water is added and the mixture is extracted with 4 × 10 ml. of chloroform. The extract is washed with water, dried and chromato- Table II

| Compound | Starting material | | Product | |
|---|---|---|---|---|
| | $(Y)_m$ | $(X)_n$ | $(Y)_m$ | $(X)_n$ |
| 1 | H | H | H | H[a] |
| 2 | H | 4-SCF$_3$ | H | 2-SCF$_3$ |
| 3 | 4'-Cl | H | 9-Cl | H |
| 4 | 4'-SCF$_3$ | H | 9-SCF$_3$ | H |
| 5 | 4'-CN | H | 9-CN | H |
| 6 | H | 4-COCH(CH$_3$)$_2$ | H | 2-COCH(CH$_3$)$_2$ |
| 7 | H | 4-SO$_2$N(CH$_3$)$_2$ | H | 2-SO$_2$N(CH$_3$)$_2$ |
| 8 | H | 4-SO$_2$CH(CH$_3$)$_2$ | H | 2-SO$_2$CH(CH$_3$)$_2$ |
| 9 | H | 4-Cl | H | 2-Cl |
| 10 | 4'-Br | H | 9-Br (m.p. 210–214° C.(dec.)) | H |
| 11 | H | 4-NO$_2$ | H | 2-NO$_2$ |
| 12 | 4'-OCH$_3$ | H | 9-OCH$_3$ | H |
| 13 | 4'-CF$_3$ | H | 9-CF$_3$ | H |

[a]m.p. 113–114° C.

EXAMPLE 2

2-Cyano-11H-pyrrolo[2,1-b][3]benzazepin-11-one

Step A: Preparation of trans-4-cyano-N-styrylpyrrole-2-carbonyl chloride

A mixture of 2.4 g. of trans-2-carboxy-4-cyano-N-styrylpyrrole (from Example 1) and 10 ml. of thionyl chloride was refluxed for 15 minutes, concentrated to dryness, treated with 10 ml. of toluene and concentrated to dryness to give 2.45 g. (95%) of trans-4-cyano-N-styrylpyrrole-2-carbonyl chloride, m.p. 119°–121° C.

Step B: Preparation of 4-cyano-N-(1,2-dichloro-2-phenylethyl)pyrrole-2-carbonyl chloride A solution of 256.5 mg. of trans-4-cyano-N-styrylpyrrole-2-carbonyl chloride in 5 ml. of chloroform was treated with 1 mmole of chlorine dissolved in 1 ml. of carbon tetrachloride. After 15 minutes, it was evaporated to dryness, treated with 5 ml. of carbon tetrachloride, and evaporated to dryness to give 307 mg. (94%) of oily 4-cyano-N-(1,2-dichloro-2-phenylethyl)pyrrole-2-carbonyl chloride.

graphed on 10 g. of silica gel by elution with benzene:ethyl acetate (3:1 v/v). The first fraction provided 47 mg. (33%) of 2-cyano-5,6-dichloro-6,11-dihydro-5H-[2,1-b] [3]benzazapin-11-one, m.p. 213°–223° C.

Step D: Preparation of 2-cyano-11H-pyrrolo[2,1-b] [3]benzazepin-11-one

Chromous chloride prepared under nitrogen from 30 mg. of 100 mesh chromium and 0.1 ml. of concentrated hydrochloric acid in 0.4 ml. of water, was added to 20 mg. of 2-cyano-5,6-dichloro-6,11-dihydro-5H-pyrrolo[2,1-b] [3]-benzazepin-11-one in 0.1 ml. of acetone at 70° C. The mixture is poured into 5 ml. of water and extracted with 3 × 3 ml. of chloroform. The chloroform is washed with water, dried and concentrated to dryness to give 13 mg. (86%) of 2-cyano-11H-pyrrolo[2,1-b] [3]benzazapin-11-one, m.p. 197° C.

Following the procedure substantially as described in Example 2 steps A, B, C, and D, but substituting for the trans-2-carboxy-4-cyano-N-styrylpyrrole used in step A thereof the trans-2-carboxy-N-styrylpyrroles described in Table I, there are produced in sequence the carbonyl chlorides, N-(1,2-dichloro-2-phenylethyl)pyrrole carbonyl chlorides, 5,6-dichloro-ketones, and 11H-pyrrolo[2,1-b][3]benzazapin-11-ones described in Table III by the following procedure:

Table III

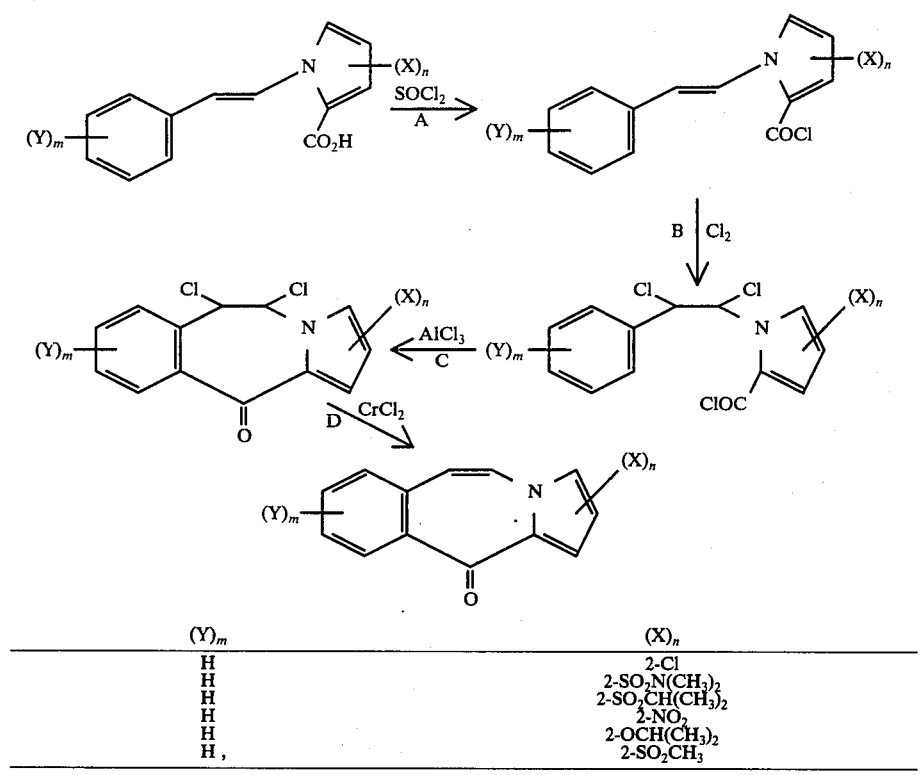

| (Y)$_m$ | (X)$_n$ |
|---|---|
| H | 2-Cl |
| H | 2-SO$_2$N(CH$_3$)$_2$ |
| H | 2-SO$_2$CH(CH$_3$)$_2$ |
| H | 2-NO$_2$ |
| H | 2-OCH(CH$_3$)$_2$ |
| H, | 2-SO$_2$CH$_3$ |

EXAMPLE 3

2-Cyano-11H-pyrrolo[2,1-b][3]benzazepin-11-one
Method I

Step A: Preparation of methyl 4-cyano-N-phenacylpyrrole-2-carboxylate

A mixture of 2 g. of methyl 4-cyanopyrrole-2-carboxylate, 2.7 g. of potassium carbonate, 2.7 g. of phenacylbromide and 15 ml. of dimethyl formamide was heated at 100° C. for 30 minutes. The mixture was poured into 200 ml. of water and extracted twice with ether. The extract was washed with water, dried and concentrated to dryness. The residue was triturated with petroleum ether to give 3 g. (84%) of methyl 4-cyano-N-phenacylpyrrole-2-carboxylate, m.p. 169°–172° C.

Step B: Preparation of 4-cyano-N-(2-chloro-2-phenethyl)pyrrole-2-carbonyl chloride A mixture of 270 mg. of methyl 4-cyano-N-phenacyl-pyrrole-2-carboxylate, 0.2 ml. of 6N sodium hydroxide solution and 5 ml. of ethanol was refluxed for 1 hour and the mixture was concentrated to a dry residue of 298 mg.

The residue was taken up in 5 ml. of aqueous ethanol (1:1 v/v) and treated with 40 mg. of sodium borohydride at room temperature for 30 minutes. The mixture was concentrated to dryness.

The residue (351 mg.) was treated with 2 ml. of phosphorus oxychloride and 400 mg. of phosphorus pentachloride and heated at 110° C. for 18 hours. The mixture was concentrated to dryness, the residue was dissolved in 25 ml. of chloroform, washed with 2 × 20 ml. of water, dried and concentrated to dryness. The residue was chromatographed on 5 g. of silica gel by elution with benzeneethylacetate (1:1 v/v). Concentration of the appropriate eluate provided 277 mg. of oily 4-cyano-N-(2-chloro-2-phenethyl)pyrrole-2-carbonyl chloride whose nmr and I.R. spectrum confirmed the structure.

Following the procedure substantially as described in Example 3, Method I, Steps A and B, but substituting for the starting material employed therein, equimolecular amounts of the methylpyrrole-2-carboxylates described in Table IV in Step A thereof, there are produced the N-(2-chloro-2-phenylethyl)pyrrole-2-carbonyl chlories also described in Table IV by the following process.

Table IV

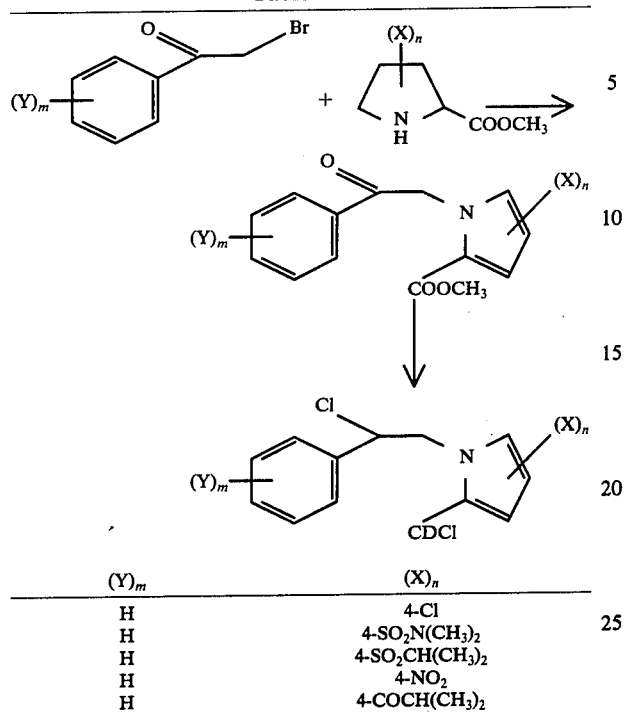

| (Y)$_m$ | (X)$_n$ |
|---|---|
| H | 4-Cl |
| H | 4-SO$_2$N(CH$_3$)$_2$ |
| H | 4-SO$_2$CH(CH$_3$)$_2$ |
| H | 4-NO$_2$ |
| H | 4-COCH(CH$_3$)$_2$ |

Method II

Step A: Preparation of 4-cyano-N-(2-hydroxy-2-phenylethyl)-pyrrole-2-carboxylic acid lactone Following the procedure of Example 1, Step A, but substituting for the sodium hydride employed therein, a catalytic amount of potassium t-butoxide, there is produced 4-cyano-N-(2-hydroxy-2-phenylethyl)pyrrole-2-carboxylic acid lactone.

Step B: Preparation of 4-cyano-N-(2-chloro-2-phenylethyl)-pyrrole-2-carbonyl chloride A mixture of 0.54 g. of lactone from Example 3, Method II, Step A, 1 g. of phosphorus pentachloride and 5 ml. of phosphorus oxychloride is refluxed for 36 hours. The volatiles were removed in vacuo, and the residue was flushed three times by vacuum distillation of toluene to give 0.54 g. (93%) of 4-cyano-N-(2-chloro-2-phenylethyl)-pyrrole-2-carbonyl chloride.

Following the procedure substantially as described in Example 3, Method B, Steps A and B but substituting for the methyl 4-cyanopyrrole-2-carboxylate used in Step A, thereof an equimolecular amount of the methyl pyrrole-2-carboxylates described in Table IV, there are produced the N-(2-chloro-2-phenylethyl)pyrrole-2-carbonyl chlorides also described in Table IV, by the following process:

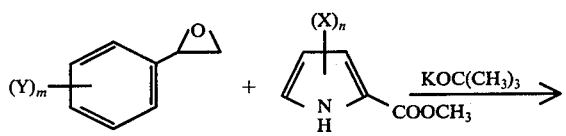

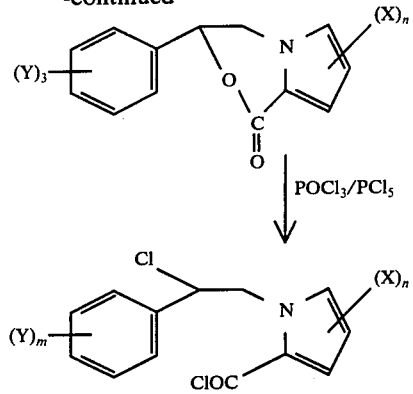

Step C: Preparation of 2-cyano-11H-pyrrolo[2,1-b][3]benzazepin-11-one

Following the procedure substantially as described in Example 2, Step C, but substituting for the starting material employed therein, an equimolecular amount of 4-cyano-N-(2-chloro-2-phenylethyl)pyrrole-2-carbonyl chloride, there is produced 6-chloro-2-cyano-6,11-dihydro-5H-pyrrolo[2,1-b][3]benzazepin-11-one. This material was dissolved in 5 ml. of ethanol containing 2 pellets of potassium hydroxide and refluxed for 15 minutes. The ethanol was evaporated. The residue was partitioned between water and chloroform. The chloroform was washed with water, dried and evaporated to dryness to give 109 mg. of crude product. This was chromatographed on 10 g. of silica gel by elution with benzene:ethyl acetate (3:1 v/v) to provide pure 2-cyano-11H-pyrrolo[2,1-b][3]benzazepin-11-one, m.p. 197° C.

Following the procedure of Example 3, Step C, but substituting for the starting material used therein an equimolecular amount of the carbonyl chlorides from Table IV, there are produced the ketones of Table V by the following process:

Table V

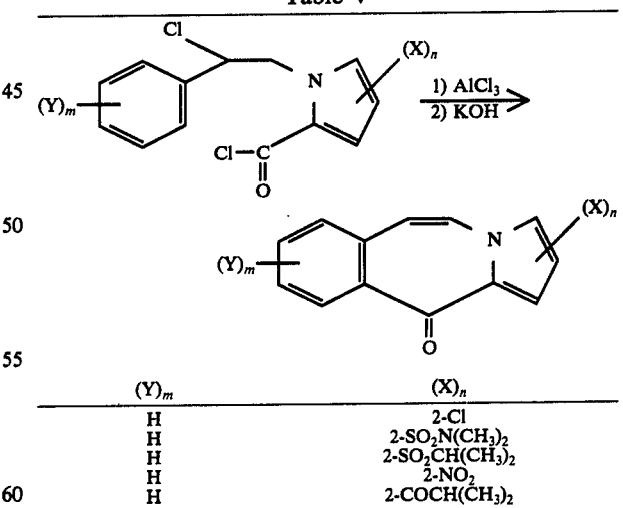

| (Y)$_m$ | (X)$_n$ |
|---|---|
| H | 2-Cl |
| H | 2-SO$_2$N(CH$_3$)$_2$ |
| H | 2-SO$_2$CH(CH$_3$)$_2$ |
| H | 2-NO$_2$ |
| H | 2-COCH(CH$_3$)$_2$ |

EXAMPLE 4

3-Trifluoromethylthio-11H-pyrrolo[2,1-b][3]benzazepin-11-one

A mixture of 100 mg. of 11H-pyrrolo[2,1-b][3]-benzazepin-11-one, 100 mg. of pyridine, and 1.5 ml. of chloroform, and 1 meq. of trifluoromethylsulfenyl chloride after 200 minutes at 45° C. was poured into water. The organic phase was washed with dilute hydrochloric acid, water, dried and concentrated to dryness. The residue on recrystallization from ether gave 124 mg. of 3-trifluoromethylthio-11H-pyrrolo[2,1-b][3]benzazepin-11-one, m.p. 137°–137.5° C.

EXAMPLE 5

2-Pentanoyl-11H-pyrrolo[2,1-b][3]benzazepin-11-one

11H-Pyrrolo[2,1-b][3]benzazepin-11-one (1.0 g.) is dissolved in 20 ml. of methylene chloride and 2.66 g. of aluminum chloride is added with cooling. At room temperature there is added little by little 720 mg. of pentanoyl chloride. Fifteen minutes after the addition is complete the mixture is poured onto ice. The organic phase is separated, filtered, dried and concentrated to dryness. The residue is triturated with ether, collected and dried to give 2-pentanoyl-11H-pyrrolo[2,1-b][3]benzazepin-11-one.

Employing the procedure substantially as described in Example 5, but substituting for the pentanoyl chloride used therein equimolecular amounts of isobutyryl chloride or dimethylsulfamoyl chloride, there are produced 2-isobutyroyl-11H-pyrrolo[2,1-b][3]benzazepin-11-one or 2-dimethyl-sulfamoyl-11H-pyrrolo-[2,1-b][3]benzazepin-11-one. In the latter case, the reaction is conducted in nitromethane at reflux temperature.

Following the procedure of Example 5, but conducting the reaction at 100°–130° C. with excess alkanoyl chloride as solvent and without the aluminum chloride, there are produced mixtures of 2- and 3-alkanoylketones which upon chromatographic separation on silica gel provides the alkanoyl ketone products described in Example 5 as well the corresponding 3-pentanoyl- and 3-isobutyroyl- compounds.

EXAMPLE 6

2-Carbamoyl-11H-pyrrolo[2,1-b][3]benzazepin-11-one

2-Cyano-11H-pyrrolo[2,1-b][3]benzazepin-11-one (30 g., 0.135 mole) in 100 ml. of concentrated hydrochloric acid and 100 ml. of acetic acid is refluxed for 2 hours. It is then poured onto 500 ml. of water and continuously extracted with methylene chloride. The solution is left to cool to room temperature and filtered to afford 2-carbamoyl-11H-pyrrolo[2,1-b][3]benzazepin-11-one.

EXAMPLE 7

2-Carboxy-11H-pyrrolo[2,1-b] [3]benzazepine-11-one

To 2-carbamoyl-11H-pyrrolo[2,1-b][3]benzazepine-11-one (27 g., 0.112 moles) in 300 ml. of 50% sulfuric acid maintained at 50° C. is added slowly 25 g. of sodium nitrite in 75 ml. of water. At the end of the addition, the solid is filtered, washed with water and air-dried to yield 2-carboxy-11H-pyrrolo[2,1-b] [3]benzazepine-11-one.

EXAMPLE 8

2-Dimethylcarbamoyl-11H-pyrrolo[2,1-b][3]benzazepin-11-one

Step A: Preparation of 2-chlorocarbonyl-11H-pyrrolo[2,1-b][3]benzazepin-11-one 11H-11-oxo-pyrrolo[2,1-b][3]benzazepine-2-carboxylic acid (24 g., 99 mmoles) in 100 ml. of thionyl chloride is refluxed for 15 minutes. The volatiles are removed under vacuum and the residue is triturated in ether. Filtration and air drying yields 2-chlorocarbonyl-11H-pyrrolo[2,1-b][3]benzazepin-11-one.

Step B: Preparation of 2-dimethylcarbamoyl-11H-pyrrolo[2,1-b][3]benzazepine-11-one Anhydrous dimethyl amine is bubbled through a suspension of 2-chlorocarbonyl-11H-pyrrolo[2,1-b][3]-benzazepin-11-one (23 g., 88.5 mmoles) in 100 ml. of methylene chloride. (Note: The introduction of dimethyl amine causes the mixture to reflux and this reflux stops when all the acid chloride is reacted.)

The reaction mixture is washed with water and dried over sodium sulfate. It is then taken to dryness, triturated in ether, filtered and air-dried to yield 2-dimethylcarbamoyl-11H-pyrrolo[2,1-b][3]benzazepin-11-one.

Following the procedure of Example 8, Step B, but substituting for the dimethylamine used therein, an equimolecular amount of methylamine, there is produced 2-methylcarbamoyl-11H-pyrrolo[2,1-b][3]benzazepin-11-one.

EXAMPLE 9

2-Methoxycarbonyl-11H-pyrrolo[2,1-b][3]benzazepin-11-one

11-Oxo-11H-pyrrolo[2,1-b][3]benzazepine-2-carboxylic acid (25.5 g., 0.11 moles) in 300 ml. of methanol saturated with hydrogen chloride is refluxed until a homogeneous solution is obtained (4 hours).

The volatiles are removed under vacuum and the residue is dissolved in 300 ml. of methylene chloride, washed with dilute sodium hydroxide and then with water. It is dried over sodium sulfate and concentrated. The residue is triturated in ether, filtered and air-dried, to yield 2-methoxycarbonyl-11H-pyrrolo[2,1-b][3]benzazepine-11-one.

EXAMPLE 10

9-Trifluoromethylthio-11H-pyrrolo[2,1-b][3]benzazepin-11-one

A mixture of 42.56 g. of bis(trifluoromethylthio)mercury, 17.27 g. of 9-bromo-11H-pyrrolo[2,1-b][3]benzazepin-11-one, 28 g. of electrolytic copper dust, 98 ml. of quinoline and 84 ml. of pyridine is stirred and heated at 195° C. for 18 hours. The mixture is shaken with 400 ml. of 6N hydrochloric acid and 400 ml. benzene. The organic phase is washed with 5 × 300 ml. of 3N hydrochloric acid and 5 × 300 ml. of water, dried over magnesium sulfate, filtered and concentrated to dryness, to 9-trifluoromethylthio-11H-pyrrolo[2,1-b][3]benzazepin-11-one.

EXAMPLE 11

Preparation of 2-formyl-11H-pyrrolo[2,1-b][3]benzazepin-11-one

2-Cyano-11H-pyrrolo[2,1-b][3]benzazepin-11-one (222 mg.) and 222 mg. nickel-aluminum alloy in 2 ml. 75% formic acid is refluxed for 1½ hours. The solid is filtered off and washed with ethanol. The filtrate is diluted with 50 ml. water and extracted twice with 50 ml. methylene chloride. The organic layer is washed with water, 5% sodium bicarbonate and with water; it is then dried over magnesium sulfate and evaporated to dryness. Addition of ether induces crystallization and the crystals are filtered and air-dried to yield 2-formyl-11H-pyrrolo[2,1-b][3]benzazepin-11-one.

Using substantially the procedure described in Example 11, but starting with 9-cyano-11H-pyrrolo[2,1-b][3]benzazepin-11-one in place of the 2-cyano compound, there is obtained 9-formyl-11H-pyrrolo[2,1-b][3]benzazepin-11-one.

EXAMPLE 12

9-Cyano-11H-pyrrolo[2,1-b][3]benzazepin-11-one

A stirred mixture of 1 gm. of 9-bromo-11H-pyrrolo[2,1-b][3]benzazepin-11-one, 1 gm. of cuprous cyanide and 5 ml. of dimethylformamide is heated to reflux for 5 hr. The mixture is then poured into a solution of 4 gm. of ferric chloride hydrate in 25 ml. of 2N hydrochloric acid. After stirring the resulting mixture at 60° for 30 min., it is extracted with 3 × 50 ml. of ethyl acetate, the organic extracts washed with 3 × 100 ml. of water and dried over Na₂SO₄. Evaporation of the dried solution yields 9-cyano-11H-pyrrolo[2,1-b][3]benzazepin-11-one.

EXAMPLE 13

2-Hydroxymethyl-11H-pyrrolo[2,1-b][3]benzazepin-11-one

A solution of 2.23 gm. of 2-formyl-11H-pyrrolo-[2,1-b][3]benzazepin-11H-one and 95 mg. of sodium borohydride in 20 ml. of ethanol is stirred at 25° C. for 2 hrs. The solvent is evaporated and the residue dissolved in methylene chloride to extract the crude product from inorganic materials. After chromatography on silica gel, there is obtained 2-hydroxymethyl-11H-pyrrolo[2,1-b][3]benzazepin-11-one.

EXAMPLE 14

2-Trifluoromethyl-11H-pyrrolo[2,1-b][3]benzazepin-11-one

In a sealed Hasteloy-C lined pressure vessel a mixture of 10 gm. of 2-carboxy-11H-pyrrolo[2,1-b][3]benzazepin-11-one and 15 ml. of sulfur tetrafluoride is heated at 100° for 4 hrs., then at 130° for 4 hrs. The vessel is cooled to room temperature and opened cautiously (toxic fumes!). The contents of the vessel are extracted with 300 ml. of ether and the ether solution stirred vigorously with 200 ml. of 1N sodium hydroxide for 6 hrs. The ether layer is separated, dried and evaporated and the residue chromatographed over silica gel to yield 2-trifluoromethyl-11H-pyrrolo[2,1-b][3]benzazepin-11-one.

EXAMPLE 15

9-Methylthio-11H-pyrrolo[2,1-b][3]benzazepin-11-one

A mixture of 27 gm. of 9-bromo-11H-pyrrolo-[2,1-b][3]benzazepin-11-one, 15 gm. of cuprous methylsulfide, 170 ml. of quonoline and 15 ml. of pyridine is stirred under a nitrogen atmosphere for 6 hrs. at a temperature of 195° C. The reaction mixture is cooled and poured into 500 ml. of 6N HCl containing 300 gm. of cracked ice. The resulting mixture is extracted with 3 × 200 ml. of benzene which is then filtered to remove some insoluble black material. The benzene extracts are washed with 3N HCl until the aqueous layer remains acidic, then washed with 100 ml. H₂O, dried (Na₂SO₄) and evaporated to yield 9-methylthio-11H-pyrrolo[2,1-b][3]benzazepin-11-one.

Following the above procedure of Example 15 but replacing cuprous methylsulfide by cuprous isopropylsulfide, there is obtained 9-isopropylthio-11H-pyrrolo[2,1-b][3]benzazepin-11-one.

EXAMPLE 16

2-Trifluoromethylsulfinyl-11H-pyrrolo[2,1-b][3]benzazepin-11-one

A solution of 3gm. of 2-trifluoromethylthio-11H-pyrrolo[2,1-b][3]benzazepin-11-one in 25 ml. of acetic acid containing 3 ml. of 50% hydrogen peroxide is stirred at 25° C. for 6 hrs. The solvent is evaporated and the residue dissolved in 100 ml. of methylene chloride. The solution is washed with 2 × 25 ml. of 5% Na₂CO₃ solution, dried and evaporated. Chromatography of the residue on silica gel yields 2-trifluoromethylsulfinyl-11H-pyrrolo[2,1-b][3]benzazepin-11-one.

Using the procedure of Example 16 but starting with 9-methylthio-11H-pyrrolo[2,1-b][3]benzazepin-11-one, there is obtained 9-methylsulfinyl-11H-pyrrolo[2,1-b][3]benzazepin-11-one.

Similarly, 9-isopropylthio-11H-pyrrolo[2,1-b][3]benzazepin-11-one, using the procedure of Example 16, produces 9-isopropylsulfinyl-11H-pyrrolo[2,1-b][3]benzazepin-11-one.

EXAMPLE 17

2-Trifluoromethylsulfonyl-11H-pyrrolo[2,1-b][3]benzazepin-11-one

A solution of 2 gm. of 2-trifluoromethylsulfinyl-11H-pyrrolo[2,1-b][3]benzazepin-11-one in 20 ml. of acetic acid containing 5 ml. of 90% hydrogen peroxide is stirred at 25° C. for 4 days. The solvent is evaporated and the residue dissolved in 100 ml. of methylene chloride. After washing the organic solution with 2 × 25 ml. of 1N Na₂CO₃, it is dried and evaporated, and the residue chromatographed on silica gel to yield 2-trifluoromethylthio-11H-pyrrolobenzazepin-11-one.

Using the procedure of Example 17 but starting with 9-methylsulfinyl-11H-pyrrolo[2,1-b][3]benzazepin-11-one there is prepared 9-methylsulfonyl-11H-pyrrolo[2,1-b][3]benzazepin-11-one.

Similarly using the procedure of Example 17 but starting with 9-isopropylsulfinyl-11H-pyrrolo[2,1-b][3]benzazepin-11-one there is obtained 9-isopropylsulfonyl-11H-pyrrolo[2,1-b][3]benzazepin-11-one.

EXAMPLE 18

9-Hydroxy-11H-pyrrolo[2,1-b][3]benzazepin-11-one

Ethanethiol (0.62 g., 10 mmoles), dissolved in dimethyl formamide (10 ml.) is added to a suspension of sodium hydride (0.5 g. of 50% oil dispersion) in dry dimethyl formamide (5 ml.). The mixture is stirred until all hydrogen has evolved and 9-methoxy-11H-pyrrolo[2,1-b][3]benzazepin-11-one (2.26 g., 10 mmoles) is added. The solution is refluxed for a period of 3 hours. The cooled reaction mixture is acidified with 0.2N HCl and extracted with chloroform. The organic layer is washed with water, dried over sodium sulfate and concentrated to yield 9-hydroxy-11-H-pyrrolo[2,1-b][3]benzazepin-11-one.

EXAMPLE 19

9-Carbamoyl-11-H-pyrrolo[2,1-b][3]benzazepin-11-one

9-Cyano-11H-pyrrolo[2,1-b][3]benzazepin-11-one (30 g., 0.135 mole) in 100 ml. of concentrated hydrochloric acid and 100 ml. of acetic acid is refluxed for 2 hours. It is then poured onto 500 ml. of water and continuously extracted with methylene chloride. The solution is left to cool to room temperature and filtered to afford 9-carbamoyl-11H-pyrrolo[2,1-b] [3]benzazepin-11-one.

EXAMPLE 20

9-Carboxy-11H-pyrrolo[2,1-b] [3]benzazepin-11one

To 9-carbamoyl-11H-pyrrolo[2,1-b] [3]-benzazepin-11-one (27 g., 0.112 moles) in 300 ml. of 50% sulfuric acid maintained at 50° C. is added slowly 25 g. of sodium nitrite in 75 ml. of water. At the end of the addition, the solid is filtered, washed with water and air-dried to yield 9-carboxy-11H-pyrrolo[2,1-b] [3]benzazepin-11-one.

EXAMPLE 21

9-Ethoxycarbonyl amino-11H-pyrrolo[2,1-b] [3]benzazepin-11-one

To 9-carboxy-11H-pyrrolo[2,1-b] [3]benzazepin-11-one (96 g., 0.4 moles) in 500 ml. ethanol, and is added successively triethylamine (52 g., 0.52 moles) and diphenylphosphoro azide (112 g., 0.40 mmoles). Reflux is maintained for 3 hrs. The mixture is poured onto water, extracted with ethyl acetate, washed with 1N sodium hydroxide and dried over magnesium sulfate to yield after evaporation 1.70 g. of a residue that is chromatographed on silica gel. Elution with methylene chloride yields 9-ethoxycarbonylamino-11H-pyrrolo[2,1-b] [3]benzazepin-11-one.

EXAMPLE 22

9-Amino-11H-pyrrolo[2,1-b] [3]benzazepin-11-one

To 9-ethoxycarbonyl amino-11H-pyrrolo[2,1-b] [3]benzazepin-11-one (2.80 g., 10 mmole) in 100 ml. EtOH is added 10 ml. 2N potassium hydroxide. Reflux is maintained for 42 hrs. The volatiles are removed under vacuum and the residue is extracted with chloroform, washed with water and dried over magnesium sulfate. Evaporation leaves a dark residue that is purified by chromatography on silica gel. Elution with 10% methanol in chloroform yields 9-amino-11H-pyrrolo[2,1-b] [3]benzazepin-11-one that decomposes slowly on standing.

EXAMPLE 23

9-Methylamino-11H-pyrrolo[2,1-b] [3]benzazepin-11-one

A solution of 9-amino-11H-pyrrolo[2,1-b] [3]-benzazepin-11-one in triethyl orthoformate (2.17 g., 10 mmoles in 80 ml.) is refluxed for 5 hrs. The volatiles are removed under vacuum and the residue, dissolved in 100 ml. absolute ethanol is stirred in an ice bath as sodium borohydride (0.88 g., 0.024 moles) is added over a period of 10 minutes. The mixture is stirred for a period of 2 hrs. After concentration of the ethanol, the residue is dissolved in ethyl acetate, washed with water, dried over Na$_2$SO$_4$ and concentrated to dryness to yield 9-methylamino-11H-pyrrolo[2,1-b] [3]benzazepin-11-one as a brown amorphous solid.

EXAMPLE 24

9-Dimethylamino-11H-pyrrolo[2,1-b] [3]benzazepin-11-one

To a solution of 9-amino-11H-pyrrolo[2,1-b] [3]-benzazepin-11-one (2.1 g., 10 mmoles) and 4 ml. (50 mmole) of 37% aqueous formaldehyde in 15 ml. of acetonitrile is added 1 g. (16 mmoles) of sodium cyano borohydride. A vigorous and exothermic reaction takes place and a dark residue separates. The mixture is stirred for 15 mins. and then glacial acetic acid is added dropwise until the solution tests neutral on wet pH paper. Stirring is maintained for an additional 2 hrs. The volatiles are removed under vacuum, and the residue is dissolved in chloroform. The solution is washed with base and with water, dried over sodium sulfate, and concentrated to leave a residue that is purified by chromatography on silica gel. Elution with chloroform yields 9-dimethylamino-11H-pyrrolo[2,1b] [3]benzazepin-11-one as a dark brown oil.

EXAMPLE 25

9-Acetamido-11H-pyrrolo[2,1-b] [3]benzazepin-11-one

9-Amino-11H-pyrrolo[2,1-b] [3]benzazepin-11-one (2.1 g., 11.4 mmoles) dissolved in 15 ml. pyridine is treated with acetic anhydride (2 ml.) at room temperature for 19 hours. The volatiles are removed under vacuum and the residue is dissolved in chloroform, and chromatographed on silica gel. Elution with chloroform yields 9-acetamido-11H-pyrrolo[2,1-b] [3 benzazepin-11-one.

What is claimed is:

1. A compound of structural formula:

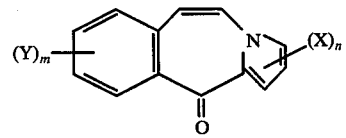

wherein
n is [3,2,] 1, or 0 (X is hydrogen);
m is [4, 3, 2,] 1 or 0 (Y is hydrogen); and
X and Y are independently selected from
(1) hydrogen,
(2) halo,
(3) formyl,
(4) lower alkanoyl,
(5) lower alkyl,
(6) lower alkoxycarbonyl,
(7) hydroxy-lower alkyl,
(8) perhalo-lower alkyl,
(9) lower alkoxy,
(10) cyano,
(11) perhalo-lower alkylthio,
(12) lower alkylthio,
(13) lower alkylsulfonyl,
(14) perhalo-lower alkylsulfonyl,
(15) lower alkylsulfinyl,
(16) perhalo-alkylsulfinyl,
(17) amino,
(18) lower alkanoylamino,
(19) lower alkylamino,
(20) di(lower alkyl)amino,
(21) hydroxy,
(22) N-lower alkylcarbamoyl,
(23) N,N-di(lower alkyl)carbamoyl,
(24) nitro,
(25) di(lower alkyl)sulfamoyl,
(26) lower alkoxycarbonylamino,
(27) N-loweralkyl-carbamoyloxy,
(28) carboxy, and
(29) carbamoyl.

2. 9-Chloro-11H-pyrrolo[2,1-b] [3]benzazepin-11-one.

3. The compound of claim 1 of structural formula:

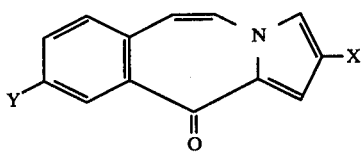

wherein X and Y are as defined therein.

4. The compound of claim 3, wherein one of X and Y is hydrogen and the other is hydrogen, cyano, or $C_{2-6}$ alkanoyl.

5. The compound of claim 4, which is 11H-pyrrolo[2,1-b] [3]benzazepin-11-one.

6. The compound of claim 4, which is 2-cyano-11H-pyrrolo[2,1-b] [3]benzazepin-11-one.

7. The compound of claim 4, which is 2-pentanoyl-11H-pyrrolo[2,1-b] [3]benzazepin-11-one.

* * * * *

UNITED STATES PATENT OFFICE
CERTIFICATE OF CORRECTION

Patent No. 4,056,536          Dated November 1, 1977

Inventor(s) Joseph G. Atkinson et al.

It is certified that error appears in the above-identified patent and that said Letters Patent are hereby corrected as shown below:

Claim 1, column 18, line 37; "n is [3,2,]1, or 0 (X is hydrogen); should be --- n is 1, or 0 (X is hydrogen); ---

Claim 1, column 18, line 38; "m is [4,3,2,]1 or 0 (Y is hydrogen); and" should be --- m is 1 or 0 (Y is hydrogen); and ---.

Signed and Sealed this

*Thirteenth* Day of *June 1978*

[SEAL]

*Attest:*

RUTH C. MASON
*Attesting Officer*

DONALD W. BANNER
*Commissioner of Patents and Trademarks*